United States Patent
Fischer et al.

(10) Patent No.: US 7,594,439 B2
(45) Date of Patent: Sep. 29, 2009

(54) METHOD AND DEVICE FOR ULTRASONIC TESTING OF A WORKPIECE HAVING AN UNEVEN SURFACE

(75) Inventors: Eberhard Fischer, Röttenbach (DE); Rainer Meier, Erlangen (DE); Friedrich Mohr, Nürnberg (DE)

(73) Assignee: intelligeNDT Systems & Servises GmbH, Erlangen (DE)

( * ) Notice: Subject to any disclaimer, the term of this patent is extended or adjusted under 35 U.S.C. 154(b) by 228 days.

(21) Appl. No.: 11/518,846

(22) Filed: Sep. 11, 2006

(65) Prior Publication Data

US 2007/0056373 A1 Mar. 15, 2007

(30) Foreign Application Priority Data

Sep. 10, 2005 (DE) .................. 10 2005 043 122

(51) Int. Cl.
*G01N 29/26* (2006.01)
*G01N 29/06* (2006.01)

(52) U.S. Cl. .................. 73/626; 73/628; 73/634

(58) Field of Classification Search .......... 73/620, 73/634
See application file for complete search history.

(56) References Cited

U.S. PATENT DOCUMENTS

| | | | | |
|---|---|---|---|---|
| 3,978,714 A | * | 9/1976 | Shraiber et al. | 73/625 |
| 4,010,635 A | * | 3/1977 | Patsey | 73/644 |
| 4,237,902 A | | 12/1980 | Okazaki | |
| 4,252,022 A | * | 2/1981 | Hurwitz | 73/582 |
| 4,471,785 A | * | 9/1984 | Wilson et al. | 600/447 |
| 4,537,075 A | * | 8/1985 | Jackson et al. | 73/634 |
| 5,024,094 A | | 6/1991 | Kubota et al. | |
| 5,214,616 A | * | 5/1993 | Terhune et al. | 367/99 |
| 5,301,552 A | * | 4/1994 | Nagura et al. | 73/606 |
| 5,335,547 A | * | 8/1994 | Nakajima et al. | 73/622 |

(Continued)

FOREIGN PATENT DOCUMENTS

DE   10 2004 027 305 A1   3/2005

(Continued)

OTHER PUBLICATIONS

Roy et al.: Control of the ultrasonic beam transmitted through an irregular profile using a smart flexible transducer: modelling and application, pp. 243- 246, Elsevier Science, B.V., 2002.

*Primary Examiner*—Hezron Williams
*Assistant Examiner*—Rose M Miller
(74) *Attorney, Agent, or Firm*—Laurence A. Greenberg; Werner H. Stemer; Ralph E. Locher (57) ABSTRACT

A method and a device for the ultrasonic testing of a workpiece having an uneven surface is provided. An ultrasonic test head containing a multiplicity of transducer elements arranged rigidly in a linear array, is acoustically coupled to a workpiece. The ultrasonic test head can be driven in a time-delayed manner with a delay time predetermined for each transducer element. The propagation time of an ultrasonic signal transmitted by an individual transducer element and reflected from the surface and received by this transducer element is measured for a number of the transducer elements and is used for correcting the delay times. The transducer elements are subsequently driven with these corrected delay times.

6 Claims, 5 Drawing Sheets

U.S. PATENT DOCUMENTS

| | | | |
|---|---|---|---|
| 5,497,662 A * | 3/1996 | Dykes | 73/634 |
| 5,549,002 A * | 8/1996 | Howard et al. | 73/602 |
| 2002/0088282 A1 * | 7/2002 | Zayicek et al. | 73/628 |
| 2004/0245315 A1 | 12/2004 | Maev et al. | |
| 2005/0126293 A1 * | 6/2005 | Dasch | 73/618 |
| 2005/0230360 A1 | 10/2005 | Maev et al. | |
| 2008/0121040 A1 * | 5/2008 | MacLauchlan et al. | 73/618 |

FOREIGN PATENT DOCUMENTS

| | | |
|---|---|---|
| GB | 2 402 485 A | 12/2004 |
| JP | 2000-65807 | 3/2000 |

* cited by examiner

METHOD AND DEVICE FOR ULTRASONIC TESTING OF A WORKPIECE HAVING AN UNEVEN SURFACE

BACKGROUND OF THE INVENTION

Field of the Invention

The invention relates to a method and device for the ultrasonic testing of a workpiece having an uneven surface.

It is particularly in the area of welded seams, that workpieces have an uneven surface at roots and cover pass which is normally ground by hand. In spite of such manual grinding, even surfaces are not reached in this process. When welding together pipes of rustproof steel, there is also strong drawing-in due to shrinkage during the cooling which causes additional unevennesses. Welded joints in pipeline systems of nuclear power stations also have starting threads at the inside diameter of pipes for adapting the inside diameter and transition slopes to the original diameter, platings on ferritic pipelines, buffer welds on the ferritic material for welding to austenitic components and transition slopes for diameter expansion on stubs. All this has the effect that the ultrasonic test sensors used for testing such a welded seam must be placed and moved on uneven irregularly wavy workpiece surfaces both in internal and external testing. An example of such an uneven or wavy surface of a workpiece is reproduced in FIG. 9. According to this figure, two parts 2a and 2b of a workpiece 2, for example a pipeline of an austenitic steel and a stub of a ferritic material, are welded together via a buffer weld 8 at a welded seam 6. Apart from unavoidable surface unevennesses, a distinct waviness is obtained in the area of the welded seam 6 and of the buffer weld 8. This waviness or unevenness has the consequence that in this zone between the surface 13 of the workpiece 2 and an ultrasonic test head 10 with a level rigid coupling face 12, an uneven gap 14 is produced which influences the acoustic irradiation conditions into the workpiece 2 and impairs or fundamentally falsifies an interpretation of the measurement results. The acoustic irradiation conditions are additionally changed by the fact that, due to the unevenness of the surface of the workpiece 2, on which, in the example shown, an offset between the two parts 2a and 2b is also superimposed, the coupling face 12 is no longer parallel to a mean straight-line surface contour 16 but oriented at an unknown angle of inclination $\alpha$ to the latter.

Figure 9:
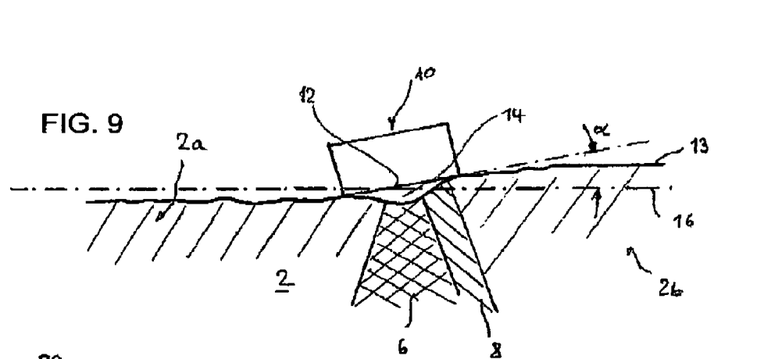
FIG. 9 shows a workpiece having an uneven surface with a test head placed in the area of a welded seam, in a diagrammatic longitudinal section.

The gap 14 is filled with a coupling medium, as a rule water. Reflections in the gap 14 between coupling face 12 and surface 13 cause interferences which can weaken the ultrasonic signal by up to about 14 dB in the worst case. In addition, the ultrasonic beam is irregularly refracted at the wavinesses of the workpiece surface and the formation of a sonic beam is prevented. This can lead to defects (reflectors) in the workpiece 2 being overlooked.

In order to solve the problems associated with this unevenness or waviness, it was attempted to perform the testing from test positions at which the surface 13 of the workpiece 2 is even, i.e., in which the test head 10 is seated as flatly as possible on the surface 13. In other words: the test head 10 was placed an offset from the welded seam 6. However, such a possibility is not practicable for a large number of applications due to the boundary conditions explained above. As an alternative, test heads are also used which are narrow in a direction parallel to the waviness—perpendicularly to the plane of the drawing in the example of FIG. 1—so that they can follow the contour of the wave when the test head is moved over the welded seam so that a distinct, irregularly shaped coupling gap 14 as shown in FIG. 9 does not arise. In order to be able to "ride" on the surface 13 in this manner, the test heads must be constructed to be very narrow. Such test heads, however, produce acoustic fields with large aperture angles which are no longer suitable for testing a workpiece with greater wall thickness, from about 30 mm in the example.

From the publication S. Mahaut et al., Pipe Inspection using UT Smart flexible Transducer, Technical Paper, 8th ECNDT Barcelona 2002, an ultrasonic test head is known, the coupling face of which is flexible and can adapt itself to the surface contour of the workpiece. To this end, the ultrasonic test head contains a multiplicity of transducer elements arranged in a row and mechanically separated from one another so that the array formed in this manner can adapt itself to the surface contour of the workpiece and has the same contour on its rear side. This rear contour is measured with an optical measuring arrangement. The individual transducer elements of the array are then driven with a delay time which is corrected in accordance with this contour in order to correctly adjust acoustic irradiation angle and depth of focus in this manner. However, the separate construction of the individual transducer elements with wearing layer, adaptation layer, piezoelectric oscillator, damping compound and electrical wiring and their mechanical suspension and water tightness is very expensive. In addition, such a test head only exhibits limited durability and ruggedness.

SUMMARY OF THE INVENTION

The invention is then based on the object of specifying a method for the ultrasonic testing of a workpiece having an uneven surface, which does not have the disadvantages mentioned above. In addition, the invention is based on the object of specifying a device operating in accordance with this method.

With respect to the method, the said object is achieved according to the invention by means of a method having the features of patent claim 1. In the method for the ultrasonic testing of a workpiece having an uneven surface with an ultrasonic test head, acoustically coupled to the workpiece, which contains a multiplicity of transducer elements arranged rigidly in a linear array, which can be driven in a time-delayed manner with a delay time predetermined for each transducer element, the propagation time of an ultrasonic signal transmitted by an individual transducer element and reflected from the surface and received by this transducer element is measured for a number of the transducer elements and is used for correcting the delay times, and the transducer elements are subsequently driven with these corrected delay times. Due to these measures, wavy workpiece surfaces can be tested with a simple and rugged construction of the ultrasonic test head.

If, in addition, an angle of inclination of the ultrasonic test head is measured with respect to a mean straight-line surface contour of the workpiece and is taken into consideration in determining the corrected delay times, inclined positions of the ultrasonic test head caused by a waviness of the surface of the workpiece can be detected and compensated for by correspondingly corrected drive of the transducer elements.

With regard to the device, the object according to the invention is achieved by means of a device having the features of patent claim 3, the advantages of which, like the advantages of its subordinate patent claims, correspond to the advantages specified in each case for the associated method claims.

For further explanation of the invention, reference is made to the exemplary embodiment of the drawing, in which:

DESCRIPTION OF THE PREFERRED EMBODIMENTS

Figures 1, 2:
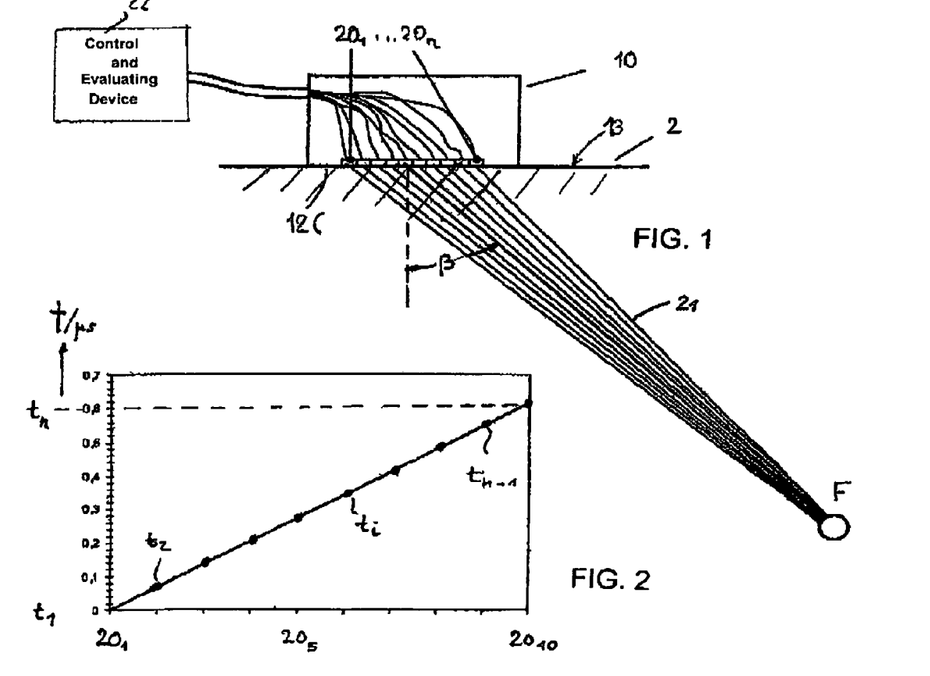
FIG. 1 shows a device according to the invention with an ultrasonic test head placed on a level workpiece in a test position, which contains a linear array of a multiplicity of transducer elements.
FIG. 2 shows a diagram in which the time delay between the transducer elements of the array is plotted against the position of the transducer elements in the array.

According to FIG. 1, the ultrasonic test head 10 of a device according to the invention contains a multiplicity n of transducer elements $20_{1, \ldots i, \ldots n}$ arranged rigidly in a linear array. Between the receiving and transmitting faces of the transducer elements $20_i$ of the array and the coupling face 12 placed directly onto the level surface 13 of the workpiece 2, a thin plane-parallel adaptation layer is located as leader segment, the thickness of which is preferably equal to half the center wavelength $\lambda/2$ or a multiple thereof of the ultrasonic signal 21 used for the testing, and the acoustic impedance of which is matched as well as possible to the acoustic impedance of a fluidic coupling medium used for the coupling, as a rule water. This thin adaptation layer is not shown in the figure for reasons of clarity.

The transducer elements $20_1$ to $20_n$ are driven by a control and evaluating device 22 with a delay time $t_1$ to $t_n$ predetermined for each transducer element $20_1$ to $20_n$ in order to adjust in this manner the angle of acoustic irradiation $\beta$ and the position of the focus F of an ultrasonic signal 21 coupled into the workpiece 2. In the example shown, there is a defect located in the area of the focus F which leads to an echo signal which is received by the transducer elements $20_1$ to $20_n$. Due to the known angle of acoustic irradiation $\beta$ and the measured propagation time of the echo signal, the defect can be located in the workpiece 2.

In FIG. 2, the delay time $t_1$ to $t_n$ is now specified in µs for the individual transducer elements $20_1$ to $20_n$, wherein 10 transducer elements $20_1$ to $20_{10}$ are provided in the example. The figure then shows that the delay times $t_i$ in a workpiece with a level surface increase between the first transducer element $20_1$ and the transducer elements $20_i$ with increasing distance of the transducer element $20_i$ from the first transducer element $20_1$. In the example shown, only one angle of acoustic irradiation $\beta$ which differs from zero is generated without focusing so that the delay times $t_i$ are on a straight line and thus the difference in delay time between in each case adjacent transducer elements $20_i$ and $20_{i\pm1}$ is constant. If electronic focusing is additionally performed, a bent curve is obtained.

Figure 3:
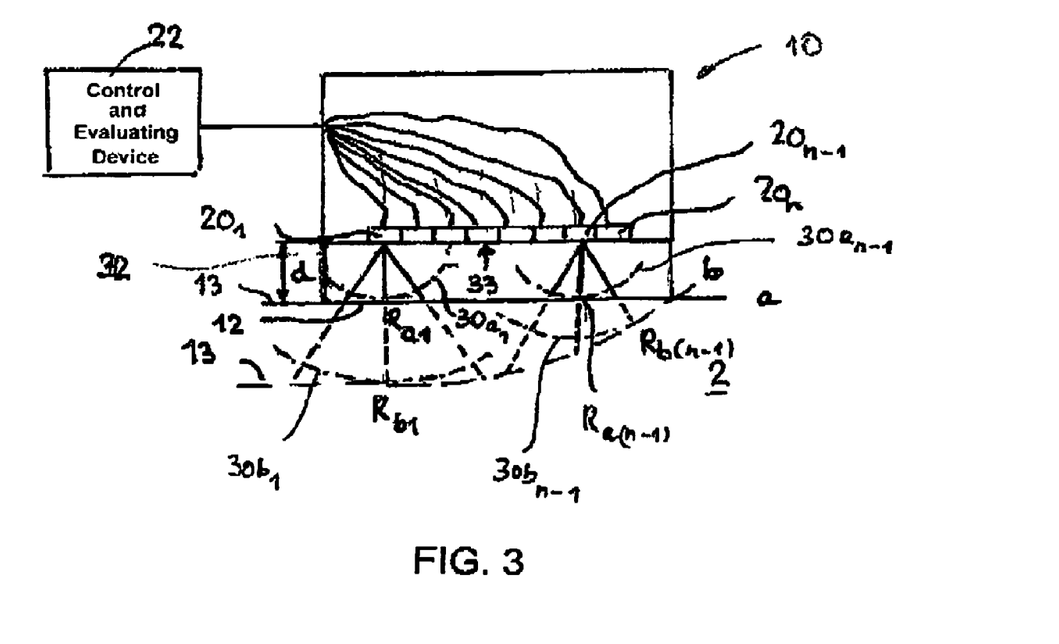
FIG. 3 shows a basic diagram for illustrating the method according to the invention.

FIG. 3 then shows two test situations in which the ultrasonic test head 10 is located above the workpiece 2 in an area with a level surface 13a (continuous surface contour) and in an area with a concavely curved surface 13b (dashed surface contour). To provide a better illustration, the distance d resulting from an adaptation layer 32 between a receiving and transmitting face 33 of the transducer elements $20_i$ and the level surface 13a of the workpiece 2 virtually coinciding with the coupling face 12 is shown exaggerated.

The transducer elements $20_1$ to $20_n$ are now driven successively in time by means of the control and evaluating device 22 in an operating mode in which they operate separately in each case in pulse-echo mode. In other words, first the transducer element $20_1$ is driven and the ultrasonic waves transmitted by this transducer element $20_1$ propagate towards the workpiece 2 with a large aperture angle. The ultrasonic waves are reflected at the surface 13a of the workpiece 2 and generate an entry echo signal. The transducer element $20_1$ essentially only receives those reflected ultrasonic waves as entry echo signal which impinge perpendicularly on the surface 13a, i.e. at point $R_{a1}$. The propagation time of this entry echo signal, i.e. of the ultrasonic signal reflected from the surface 13a and received by the transducer element $20_1$ is measured and recalculated into a distance which in the present case is equal to the distance d between receiving and transmitting face 33 and surface 13a. If the actual surface contour of the workpiece 2 in the test position is unknown, the point $R_{a1}$ of the surface of the workpiece 2 from which the received echo signals emanate could also be located on a circular arc $30a_1$ which is shown dot-dashed in the figure.

Following this, the transducer element $20_2$ is driven and the propagation time of the echo signals received by the transducer element $20_2$ is also measured. In this manner, each of the transducer elements $20_1$ to $20_n$ is driven. In the figure, the situation for the transducer element $20_{n-1}$ is also drawn for which the same conditions are obtained for the level surface 13a as for the transducer element $20_1$ (reflection of the entry echo signal in $R_{a(n-1)}$) which can be located on the circular arc $30a_{n-1}$ if the contour is not known.

In the case of the level surface 13a, the entry echo signal reaches each transducer element $20_1$ to $20_n$ after the same propagation time which is needed for traveling twice the distance d between transmitting and receiving face 33 of the transducer elements $20_1$ to $20_n$ and surface 13a.

A situation is then drawn dashed which is obtained when a concavely curved surface 13b is present. The figure shows that in this case the transducer element $20_1$ receives an entry echo signal for an ultrasonic wave emitted perpendicularly to the transmitting face from point $R_{b1}$. However, assuming a lack of knowledge of the actual surface contour, here, too, the entry echo signals can come from points which are located on the circular arc $30b_1$. In the example shown, the transducer element $20_{n-1}$ now receives the entry echo signal from a point $R_{b(n-1)}$ of the surface 13b which is not in the direction of the normal of the transducer element $20_{n-1}$. Here, too, however, the entry echo signals can come from points which are located on the circular arc $30b_{n-1}$.

Figure 4:
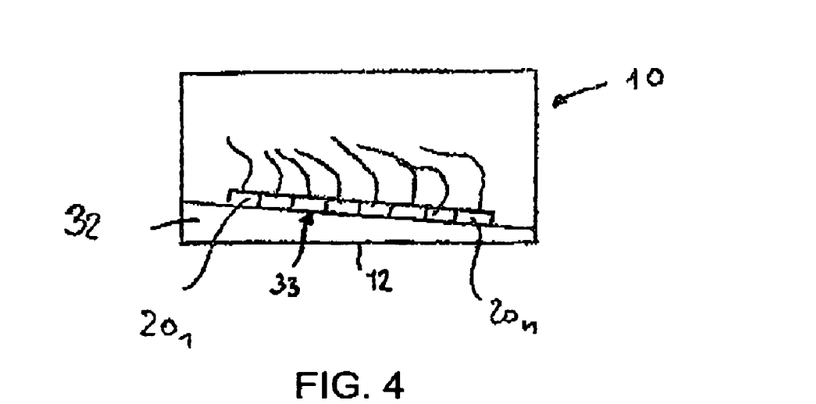
FIG. 4 shows an advantageous embodiment of an ultrasonic test head according to the invention, also in a basic diagram, FIGS. 5 and 6 in each case show a diagram in which the information about the distance between transducer element and surface of the workpiece obtained for different surface contours by means of the transducer elements of the array is illustrated.
Figure 5:
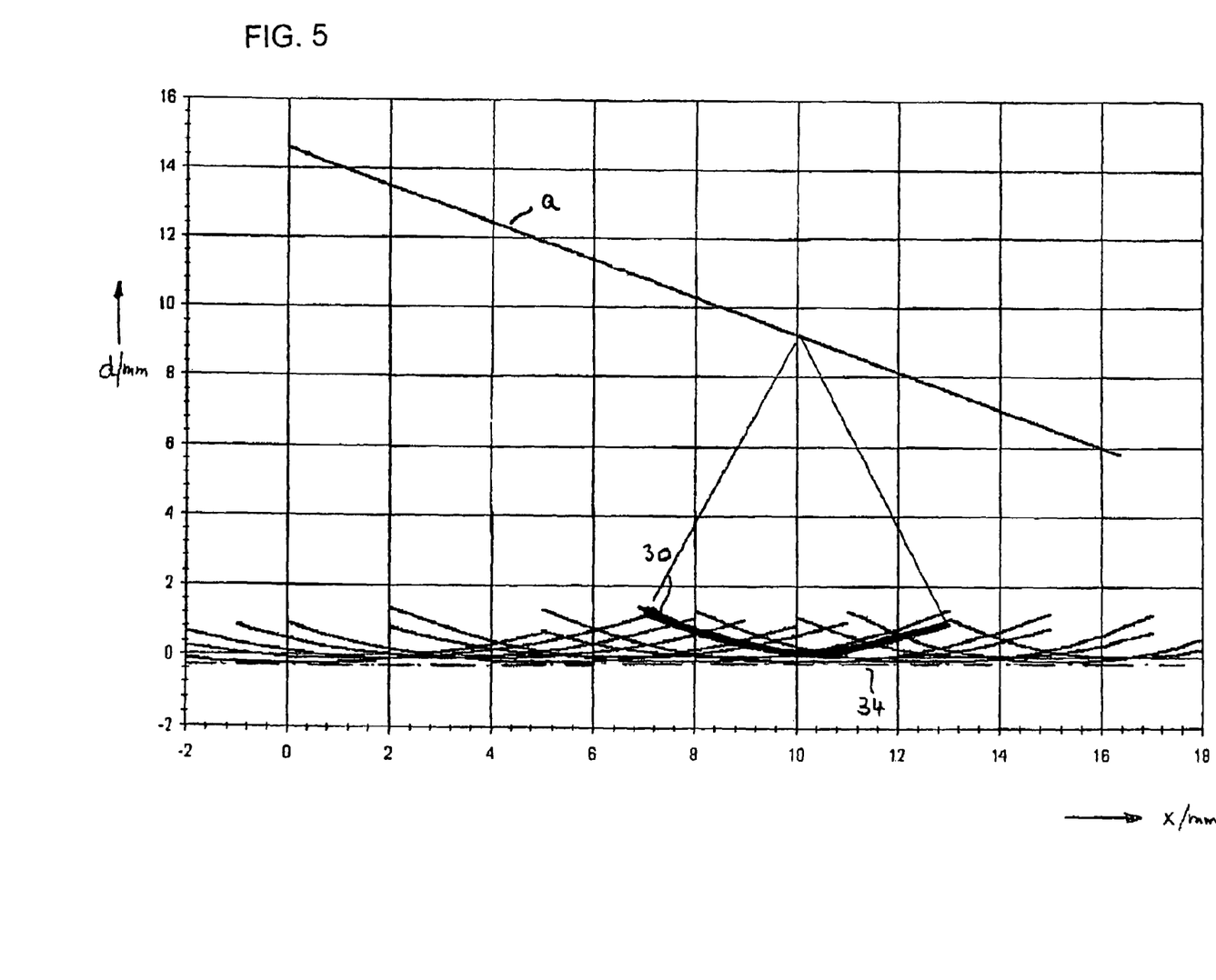

FIG. 5 shows an ultrasonic test head 10 in which, instead of a plane-parallel adaptation layer as illustrated exaggeratedly in FIG. 4, a wedge-shaped leader segment or adaptation layer 32 is provided between the receiving and transmitting face 33 and the coupling face 12 in order to achieve an angle of acoustic irradiation which differs from 0° even without time delays of the transducer elements $20_1$ to $20_n$.

FIG. 5 then shows a situation obtained when a test head shown in FIG. 4 is used on a level surface. In this figure, the distance d of the surface on the receiving and transmitting face, in each case determined by means of the individual ultrasonic transducers with the aid of the propagation time of the echo signal, the velocity of sound and geometric shape of the adaptation layer and the velocity of sound of the coupling medium, is plotted against the longitudinal extent x of the array. In the example, the array is arranged on a wedge-shaped adaptation layer with a wedge angle of 28° with which it sits directly on the level surface of the workpiece. In the figure, the position of the receiving and transmitting face of the transducer elements is specified by the line a. The figure then shows that each transducer element receives an entry echo signal which can be allocated a certain distance, the direction from which the entry echo signal has been received not being determined. For this reason, an arc is allocated to each transducer element in the diagram which reproduces possible positions of the point of the surface from which the entry echo signals are received. Thus, an arc 30, which is emphasized emboldened in the figure is allocated to the transducer element which is approximately located at the position x=10 mm. Although the transducer element at the position x=10 mm detects the distance d to the surface of the workpiece which is about 9 mm in the example shown, it does not detect its direction. If then the measurements are performed in the same manner for all transducer elements, an envelope 34 can be seen along the zero line by means of the diagram which reproduces the surface contour of the workpiece which is a level workpiece in the present case.

Figure 6:
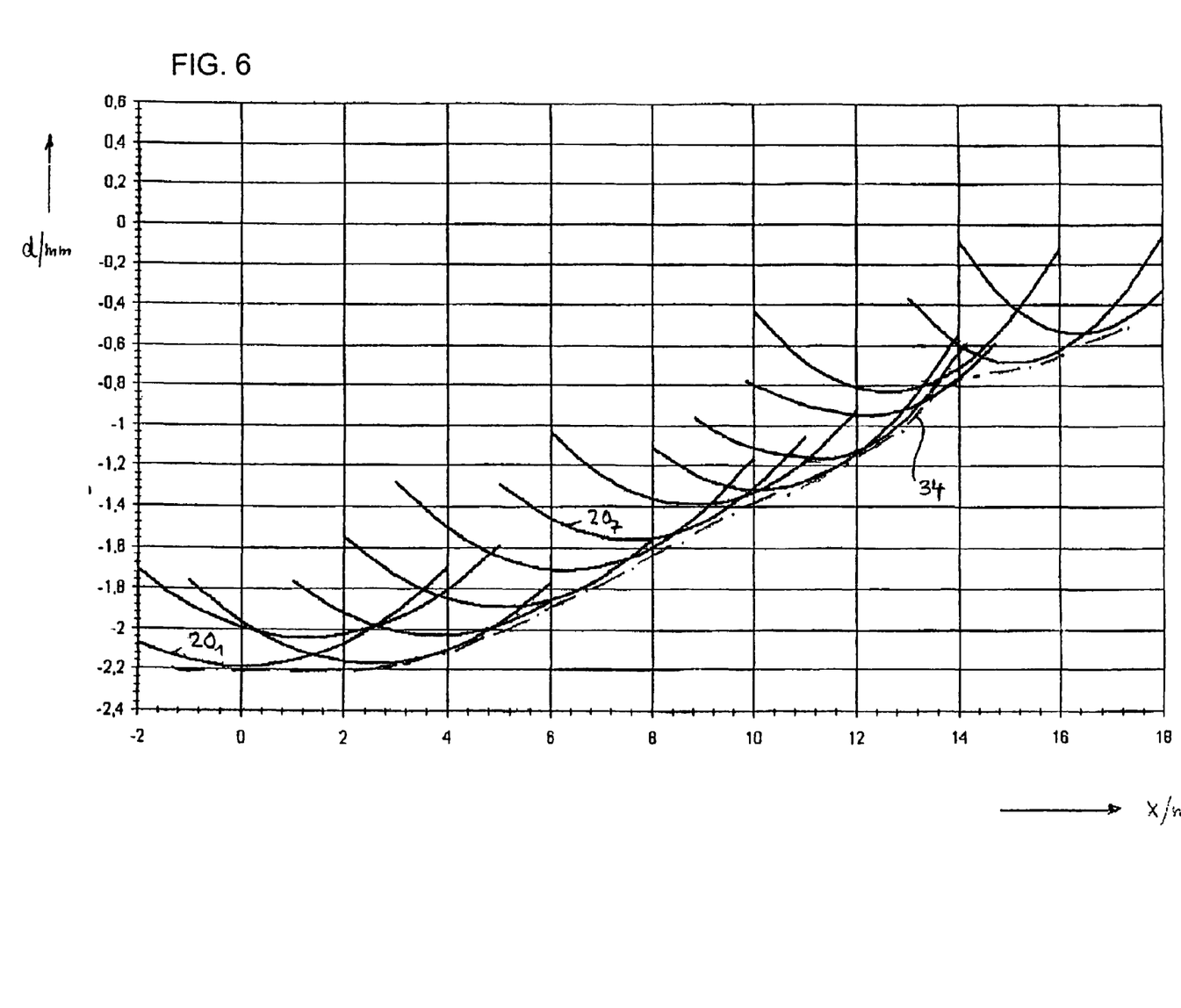

The situation is different in FIG. 6 in which the possible distance between the workpiece and the coupling face of the ultrasonic test head is also plotted against the position of the transducer elements in the ultrasonic test head. It can be seen clearly that in this case an envelope 34 is obtained which also reproduces the surface contour of the workpiece in the area of the coupling face and significantly deviates from a level surface.

This information is then used for adapting the time delay for the individual transducer elements to the different shape of the coupling gap with the aid of the control and evaluating device 22 and for adjusting the correct angle of acoustic irradiation β with respect to the mean surface contour 16. FIG. 6 shows that the surface of the workpiece is about 0.6 mm further away from the transducer element $20_1$ than from the transducer element $20_7$. With a predetermined angle of acoustic irradiation and known velocities of sound of workpiece and coupling medium and known velocity of sound and shape of an adaptation layer which may be present, the required time delay between the transducer elements $20_1$ and $20_7$ can then be calculated mathematically from this difference in distance which has been determined mathematically from the propagation time difference measured between the transducer elements $20_1$ and $20_7$ and from the angle of inclination of the surface of the workpiece resulting from the envelope 34.

Figure 7:
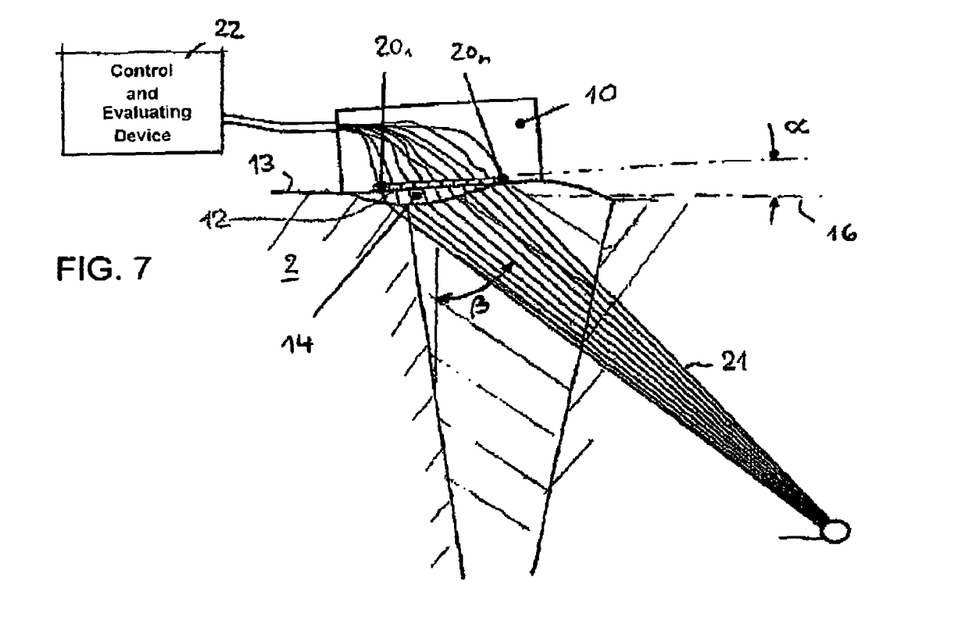
FIG. 7 shows the device according to the invention with an ultrasonic test head placed in an uneven area of the workpiece.

In this manner, the predetermined angle of acoustic irradiation β can be correctly adjusted even with a wavy surface 13 of the workpiece 2 as is shown in FIG. 7. This figure also shows that the coupling face 12 of the ultrasonic test head 10 is inclined with respect to the mean surface contour 16 by the angle of inclination α. This angle of inclination α is also detected and taken into consideration in the correction of the delay times.

Figure 8:
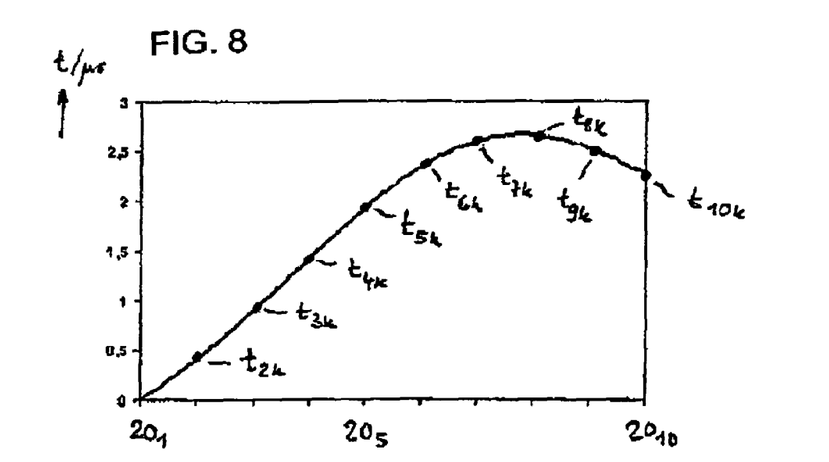
FIG. 8 shows a diagram in which the corrected time delay between the individual transducer elements of the array is plotted against the position of the transducer elements for the test situation shown in FIG. 7.

FIG. 8 then shows the corrected delay times $t_{1k}$ to $t_{10k}$ in µs for the example shown in FIG. 7 for the individual transducer elements $20_1$ to $20_{10}$. The figure shows that the profile of the corrected delay times $t_{1k}$ to $t_{10k}$ deviates significantly from the linear profile according to FIG. 3.

LIST OF REFERENCE DESIGNATIONS

2 Workpiece
2a,b Parts
6 Welded seam
8 Buffer weld
10 Ultrasonic test head
12 Coupling face
13 Surface
13a,b Level, curved surface
14 Gap
16 Mean surface contour
$20_1$ to $20_n$ Transducer element
21 Ultrasonic signal
22 Control and evaluating device
$30a_1$, $30b_1$ Circular arc
$30a_{n-1}$, $30b_{n-1}$ Circular arc
32 Adaptation layer
33 Receiving and transmitting face
34 Envelope
$R_{a1}$, $R_{b1}$ Point
$R_{a(n-1)}$, $R_{b(n-1)}$ Point
c Circular arc
d Distance
$t_1$ to $t_n$ Delay time
$t_{1k}$ to $t_{nk}$ Corrected delay time
α Angle of inclination
β Angle of acoustic irradiation

We claim:

1. A method for the ultrasonic testing of a workpiece having an uneven surface, the method comprising the steps of:
   providing an ultrasonic test head containing a multiplicity of transducer elements arranged rigidly in a linear array and being drivable in a time-delayed manner with a delay time predetermined for each transducer element;
   acoustically coupling the test head to the workpiece;
   for each of a plurality of transducer elements determining a propagation time of an ultrasonic signal transmitted by a given transducer element, reflected from the surface of the workpiece, and received by the respective given transducer element; and
   using the determined propagation times to correct the delay times of the individual transducer elements; and
   subsequently driving the transducer elements with the corrected delay times.

2. The method of claim 1, further comprising the steps of:
   measuring an angle of inclination of the ultrasonic test head with respect to a mean straight-line surface contour of the workpiece; and
   taking the measured angle of inclination into consideration when correcting the delay times.

3. A device for the ultrasonic testing of a workpiece having an uneven surface, comprising:
   an ultrasonic test head to be acoustically coupled to the workpiece, said ultrasonic test head including a multiplicity of transducer elements rigidly arranged in a linear array; and a control and evaluating device connected to said transducer elements, said control and evaluating device configured to:

drive individual transducer elements in a time-delayed manner with a delay time predetermined for each transducer element;

determine, for each of a plurality of transducer elements, a propagation time of an ultrasonic signal transmitted by a given transducer element, reflected from the surface of the workpiece, and received by the respective given transducer element; and use the determined propagation times to correct the delay times of the individual transducer elements; and drive the transducer elements with a corrected delay time determined for each transducer element.

4. The device according to claim 3, further comprising a measuring device for measuring an angle of inclination of said ultrasonic test head with respect to a mean straight-line surface contour of the workpiece.

5. The device according to claim 4, wherein said ultrasonic test head is formed with an adaptation layer between a coupling face of said ultrasonic test head and said transducer elements, said adaptation layer having an acoustic impedance matched to an acoustic impedance of a coupling fluid used for coupling said ultrasonic test head to the workpiece.

6. The device according to claim 3, wherein said ultrasonic test head is formed with an adaptation layer between a coupling face of said ultrasonic test head and said transducer elements, said adaptation layer having an acoustic impedance matched to an acoustic impedance of a coupling fluid used for coupling said ultrasonic test head to the workpiece.

* * * * *